United States Patent [19]

Wandell

[11] Patent Number: Plant 5,717

[45] Date of Patent: Apr. 15, 1986

[54] AMELANCHIER AUTUMN BRILLIANCE

[76] Inventor: Willet N. Wandell, Box 158A, R.R. #3, Urbana, Ill. 61801

[21] Appl. No.: 580,868

[22] Filed: Feb. 16, 1984

[51] Int. Cl.[4] ..... A01H 5/00

[52] U.S. Cl. ..... Plt./51

[58] Field of Search ..... Plt./51

*Primary Examiner*—Robert E. Bagwill

*Attorney, Agent, or Firm*—Wm. A. Snow

[57] ABSTRACT

This disclosure concerns a new and distinct variety of Grandiflora Amelanchier characterized by its exceptional vigorous growth habit with an abundance of pure white flowers in the spring, and thick, glossy leaves turning a brilliant red color in the fall of the year all substantially simultaneously.

4 Drawing Figures

BACKGROUND OF THE INVENTION

This new variety of Grandiflora Amelanchier was found growing in my nursery at Urbana, Ill., in a cultivated area, in a row of seedling liners. The new variety has a vigorous growth habit with thick, heavy, glossy leaves, an abundance of blooms and excellent fall color. I have approximately 300 asexually produced trees in my nursery, all of which exhibit the superior growing qualities of the parent plant.

SUMMARY OF THE INVENTION

A new and distinct cultivar of Grandiflora Amelanchier characterized by its exceptional growth habit with abundant thick, heavy, glossy leaves, an abundance of white blooms in the spring, and a brilliant red leaf in the fall, which leaves all turn substantially simultaneously, and with extreme ease of propagation even by tissue culture.

BRIEF DESCRIPTION OF THE DRAWINGS

The right hand photograph on the first sheet of drawings discloses the new variety in the spring with an abundance of white flowers. This picture was taken in May of 1983.

The left hand photograph on the first sheet of drawings is a close-up view of the flowers of the above.

The right hand photograph on the second sheet of drawings discloses the new variety in the fall. This picture was taken in November of 1983.

The left hand view on the second sheet of drawings discloses a close-up view of the red leaves of the above.

DETAILED DESCRIPTION OF THE NEW PLANT VARIETY

The following is a detailed description of my new variety of Amelanchier×grandiflora, the stated observations having been made by me in my nurseries in Urbana, Ill. The color designations are made from The Royal Horticultural Society charts except for ordinary dictionary color observations.

Origin: Seedling.

Classification: Amelanchier×grandiflora.

Parentage: A seedling of *Amelanchier laeries*×*A. arborea.*

Form: Small tree or large shrub.

Shape: Moderately spreading.

Habit: Multi-stemmed small tree or large shrub with rounded crown, heavily branched, the main stems being upright, and will reach from 15 to 25 feet in height at maturity.

Growth rate: Relatively faster than other Amelanchier.

Bark: Light gray, smooth, with fine longitudinal fissures, the under bark being light reddish brown.

Branches: Numerous, twigs measuring 3.2 mm. in diameter 2 cm. from base of terminal bud; one year twigs reddish brown, somewhat glaucous.

Leaves: Alternate, simple, deciduous; young leaves densely pubescent beneath, slightly pubescent above, bright green, folded at flowering time.

*Mature.*—Obovate or elliptical, the apices broadly acute, the margins finely denticulate nearly to base, the bases rounded or shortly-cordate glabrous above and below.

*Size.*—1 and $\frac{3}{4}$ to 2 and $\frac{1}{2}$ inches long and 1 and $\frac{1}{2}$ inches wide; mature leaves 32 to 38 mm. in thickness with cutin layer averaging 2.1 microns.

*Color.*—Medium green in summer, glossy, turning uniform brilliant red (R.H.S. 43B) in the Fall.

*Petioles.*—$\frac{3}{4}$ to $1\frac{1}{4}$ inches long, pubescent when young, glaborous at maturity.

Winter buds: Solitary, sessile, elongate, sharp pointed, mostly adpressed, reddish brown or greenish brown, $\frac{1}{3}$ to $\frac{1}{2}$ inches long; bud scales ca. 6 imbricated; leaf scars narrowly crescent-shaped with 3 bundle traces.

Fruit: Globose $\frac{1}{4}$ to $\frac{1}{3}$ inches in diameter, a berry-like pome, reddish turning dark purple or black at maturity, glaucouse, juicy, capped by persistent calyx, containing 5 or fewer seeds.

Flowers: Pure white, profuse, borne in spreading or pendulous ca. 12-flowered racemes that are $1\frac{1}{2}$ to 3 inches long; flower stalks are $\frac{1}{4}$ to $\frac{1}{2}$ inches long; petals 5, narrowly ovate ca. $\frac{3}{8}$ inches long and $\frac{1}{8}$ inches wide; calyx lobes 5, triangular, 1/16 to 3/16 inches long densely pubescent inside; floral cup densely pubescent, about as long as the calyx lobes; stamens 20; style one below, the upper one-third divided into 5 branches; each capped by a small, disk-shaped stigma; ovary inferior.

This variety clearly distinguishes from other Amelanchiers by its rapid growth, resistance to winter ice damage due to dense branching pattern and large diameter branches, profuse abundance of white flowers in the spring and absence of the tendency toward summer leaf drop due to fungus disease (*Coccomyces tumidus*) with the brilliant red fall color of the leaves almost all changing at the same time, the crown being the exception but later also turning to brilliant red versus other common Amelanchier trees which turn a variable yellow, apricot-orange or dull red fall color, the color changes being gradual.

I claim:

1. A new and distinct variety of Amelanchier × grandiflora substantially as herein shown and described, characterized by denser branching pattern so as not to be subject to winter ice damage, and no summer leaf drop due to fungus disease, and the consistent bright red fall color with a majority of the leaves turning at substantially the same time.

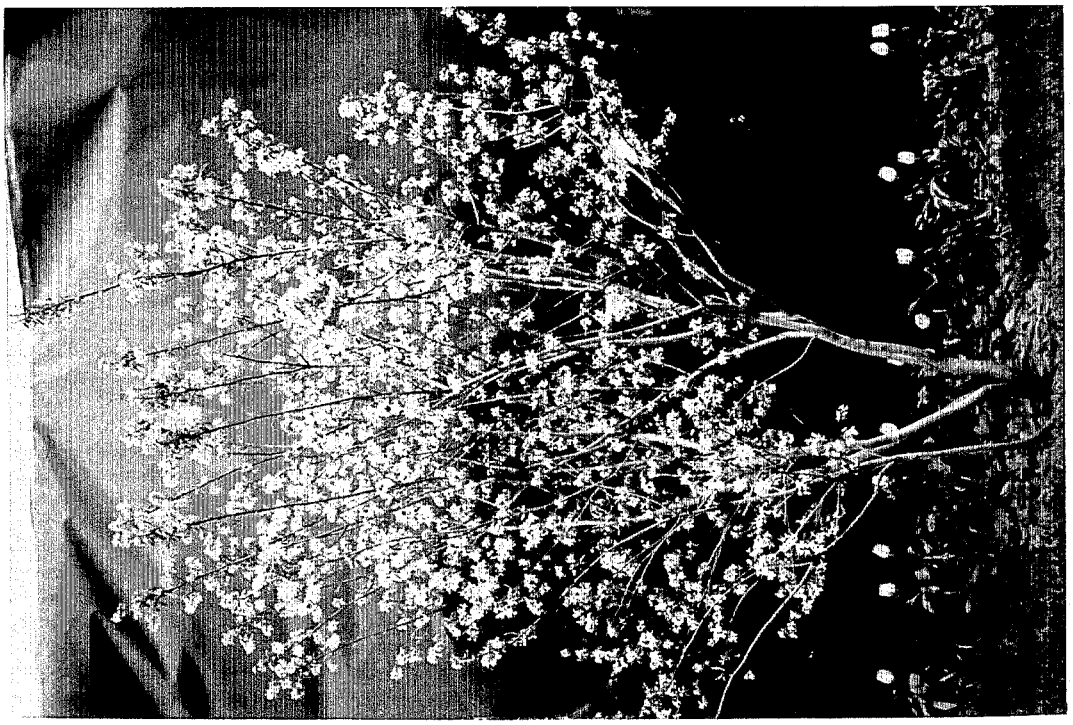
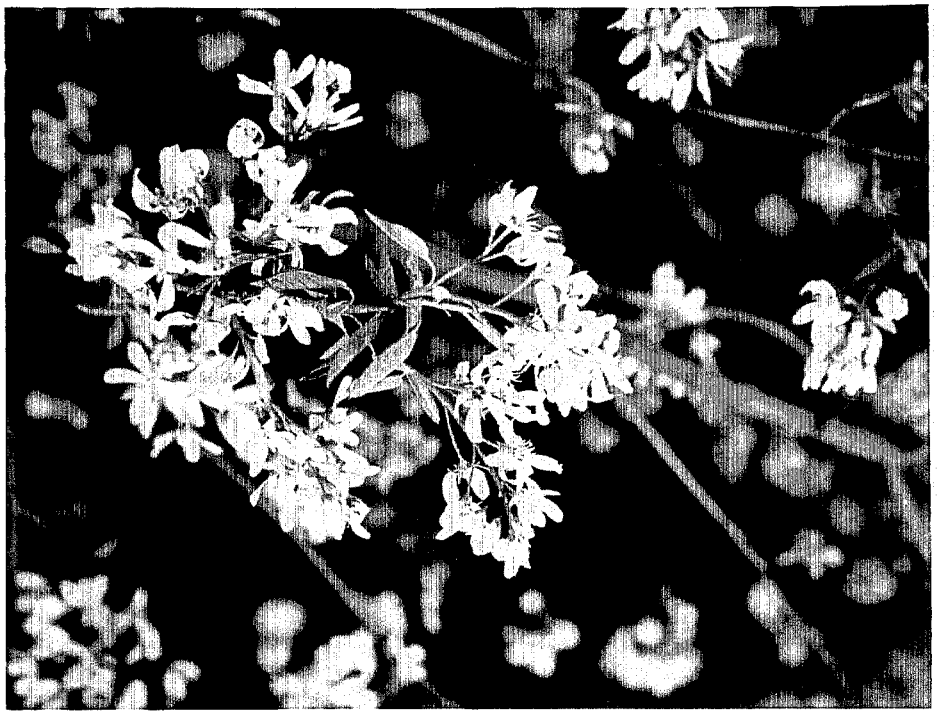

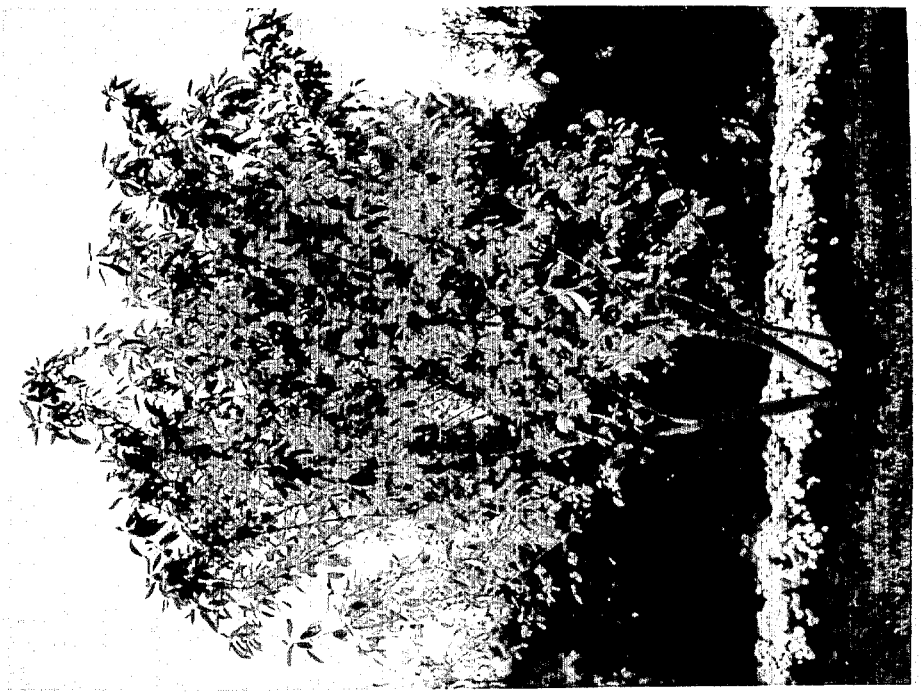
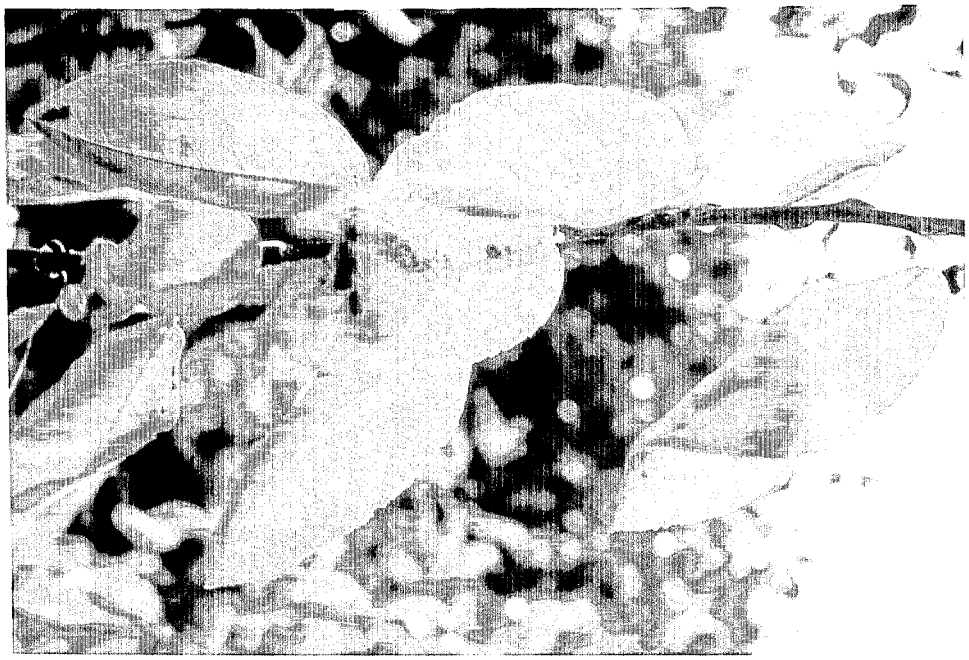

* * * * *